US008565867B2

(12) United States Patent
Armstrong et al.

(10) Patent No.: US 8,565,867 B2
(45) Date of Patent: Oct. 22, 2013

(54) CHANGEABLE ELECTRODE POLARITY STIMULATION BY AN IMPLANTABLE MEDICAL DEVICE

(75) Inventors: Randolph K. Armstrong, Houston, TX (US); Steven E. Maschino, Seabrook, TX (US); Timothy L. Scott, Sugar Land, TX (US)

(73) Assignee: Cyberonics, Inc., Houston, TX (US)

( * ) Notice: Subject to any disclaimer, the term of this patent is extended or adjusted under 35 U.S.C. 154(b) by 481 days.

(21) Appl. No.: 12/020,097

(22) Filed: Jan. 25, 2008

(65) Prior Publication Data

US 2011/0213437 A9    Sep. 1, 2011

Related U.S. Application Data

(63) Continuation-in-part of application No. 11/046,430, filed on Jan. 28, 2005, now abandoned.

(51) Int. Cl.
*A61N 1/372* (2006.01)

(52) U.S. Cl.
USPC ............................................................ 607/2

(58) Field of Classification Search
USPC .................................... 607/2, 116, 118, 139
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |

(Continued)

FOREIGN PATENT DOCUMENTS

| | | |
|---|---|---|
| CA | 2339971 | 6/2004 |
| EP | 0402683 | 12/1990 |

(Continued)

OTHER PUBLICATIONS

PCT Search Report for International Application No. PCT/US2009/000379, dated May 25, 2009; 8 pgs.

(Continued)

*Primary Examiner* — Scott Getzow
*Assistant Examiner* — Amanda Patton
(74) *Attorney, Agent, or Firm* — Cyberonics, Inc.

(57) ABSTRACT

We disclose a method of treating a medical condition in a patient using an implantable medical device including coupling at least a first electrode and a second electrode to a cranial nerve of the patient, providing a programmable electrical signal generator coupled to the first electrode and the second electrode, generating a first electrical signal with the electrical signal generator, applying the first electrical signal to the electrodes, wherein the first electrode is a cathode and the second electrode is an anode, reversing the polarity of the first electrode and the second electrode, yielding a configuration wherein the first electrode is an anode and the second electrode is a cathode, generating a second electrical signal with the electrical signal generator, applying the second electrical signal to the electrodes, reversing the polarity of the first electrode and the second electrode, yielding a configuration wherein the first electrode is a cathode and the second electrode is an anode, generating a third electrical signal with the electrical signal generator, and applying the third electrical signal to the electrodes. Each of the electrical signals can independently contain one or more pulses or one or more bursts. The number of pulses need not be equal between any two of the electrical signals.

23 Claims, 6 Drawing Sheets

(56) References Cited

U.S. PATENT DOCUMENTS

| | | |
|---|---|---|
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zarbara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 4,979,511 A | 12/1990 | Terry, Jr. ............... 128/642 |
| 5,025,807 A | 6/1991 | Zabara |
| 5,081,987 A | 1/1992 | Nigam |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. ............ 607/45 |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,531,778 A | 7/1996 | Maschino et al. ............ 607/118 |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Osorio et al. |
| 6,002,966 A | 12/1999 | Loeb et al. |
| 6,016,449 A | 1/2000 | Fischell et al. |
| 6,041,258 A | 3/2000 | Cigaina et al. |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 * | 4/2002 | DiLorenzo .................. 607/45 |
| 6,366,814 B1 | 4/2002 | Boveja |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |

(56) References Cited

U.S. PATENT DOCUMENTS

| | | |
|---|---|---|
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |

(56) References Cited

U.S. PATENT DOCUMENTS

| | | |
|---|---|---|
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby, Jr. et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja |
| 2006/0015153 A1* | 1/2006 | Gliner et al. ............ 607/45 |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja |
| 2006/0079936 A1 | 4/2006 | Boveja |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1* | 8/2006 | Armstrong et al. ............ 607/2 |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0027486 A1 | 2/2007 | Armstrong et al. |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073346 A1 | 3/2007 | Corbucci et al. |
| 2007/0073355 A1 | 3/2007 | DiLorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson et al. |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner et al. |
| 2007/0123946 A1 | 5/2007 | Masoud |
| 2007/0135855 A1 | 6/2007 | Foshee et al. |
| 2007/0142862 A1 | 6/2007 | DiLorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | DiLorenzo et al. |
| 2007/0156179 A1 | 7/2007 | Karashurov |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179558 A1 | 8/2007 | Gliner et al. |
| 2007/0179584 A1 | 8/2007 | Gliner |
| 2007/0191905 A1 | 8/2007 | Errico et al. |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |

(56) References Cited

U.S. PATENT DOCUMENTS

| | | |
|---|---|---|
| 2007/0213785 A1 | 9/2007 | Osorio et al. |
| 2007/0233192 A1 | 10/2007 | Craig |
| 2007/0233193 A1 | 10/2007 | Craig ............................... 607/2 |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0054795 A1 | 2/2009 | Misczynski et al. |
| 2009/0076567 A1 | 3/2009 | Fowler et al. |

FOREIGN PATENT DOCUMENTS

| | | |
|---|---|---|
| EP | 0713714 | 5/1996 |
| EP | 1139861 | 12/1999 |
| EP | 1070518 | 1/2001 |
| EP | 0944411 | 4/2001 |
| EP | 1145736 A2 | 10/2001 |
| EP | 1483020 | 12/2004 |
| EP | 1486232 | 12/2004 |
| EP | 1595497 | 11/2005 |
| EP | 1120130 | 12/2005 |
| EP | 1647300 | 4/2006 |
| EP | 1202775 | 9/2006 |
| GB | 2026870 | 2/1980 |
| GB | 2079610 | 1/1982 |
| WO | 9302744 | 2/1993 |
| WO | 9417771 | 8/1994 |
| WO | 0064336 A1 | 11/2000 |
| WO | 0108749 | 2/2001 |
| WO | 0064336 A9 | 6/2002 |
| WO | 03085546 | 10/2003 |
| WO | 2004036377 | 4/2004 |
| WO | 2004064918 | 8/2004 |
| WO | 2004069330 | 8/2004 |
| WO | 2004071575 | 8/2004 |
| WO | 2004075982 | 9/2004 |
| WO | 2004112894 | 12/2004 |
| WO | 2005007120 | 1/2005 |
| WO | 2005007232 | 1/2005 |
| WO | 2005028026 A1 | 3/2005 |
| WO | 2005053788 | 6/2005 |
| WO | 2005067599 | 7/2005 |
| WO | 2005101282 | 10/2005 |
| WO | 2006014760 | 2/2006 |
| WO | 2006019822 | 2/2006 |
| WO | 2006050144 | 5/2006 |
| WO | 2006122148 | 11/2006 |
| WO | 2007018793 A1 | 2/2007 |
| WO | 2007066343 A2 | 6/2007 |
| WO | 2007072425 | 6/2007 |
| WO | 2007124126 | 11/2007 |
| WO | 2007124190 | 11/2007 |
| WO | 2007124192 | 11/2007 |
| WO | 2007142523 | 12/2007 |

OTHER PUBLICATIONS

Bachman, D.,S. et al.; "Effects Of Vagal Volleys And Serotonin On Units Of Cingulate Cortex in Monkeys;" Brain Research , vol. 130 (1977). pp. 253-269.

Bohning, D.E., et al.; "Feasibility of Vagus Nerve Stimulation—Synchronized Blood Oxygenation Level-Dependent Functional MRI," A Journal of Clinical and Laboratory Research: Investigative Radiology; vol. 36, No. 8 (Aug. 2001); pp. 470-479.

Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.

Clark, K.B., et al.; "Posttraining Electrical Stimulation of Vagal Afferents with Concomitant Vagal Efferent Inactivation Enhances Memory Storage Processes in the Rat," Neurobiology of Learning and Memory, vol. 70, 364-373 (1998) Art. No. NL983863.

Clark, K.B., et al.; "Enhanced Recognition Memory Following Vagus Nerve Stimulation in Human Subjects;" Nature Neuroscience, vol. 2, No. 1, (Jan. 1999) pp. 93-98.

Craig, A.D. (BUD); "Distribution of Trigeminothalamic and Spinothalamic Lamina I Terminations in the Macaque Monkey;" The Journal of Comparative Neurology, vol. 447, pp. 119-148 (2004).

DeGiorgo, Christopher M., et al.; "Vagus Nerve Stimulation: Analysis of Device Parameters in 154 Patients During the Long-Term XE5 Study;" Epilepsia, vol. 42, No. 8; pp. 1017-1020 (2001).

(56) References Cited

OTHER PUBLICATIONS

Devous, Michael D., et al.; "Effects of Vagus Nerve Stimulation on Regional Cerebral Blood Flow in Treatment-Resistant Depression," National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Hallowitz, R.A., et al.; "Effects Of Vagal Tolleys On Units Of Intralaminar and Juxtalaminar Thalamic Nuclei in Monkeys;" Brain Research, vol. 130 (1977), pp. 271-286.

Harry, J.D., et al.; "Balancing Act: Noise is the Key to Restoring the Body's Sense of Equilibrium;" IEEE Spectrum (Apr. 2005)pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1988).

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychiatry, (May 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Lockard et al., "Feasibility And Safety Of Vagal Stimulation In Monkey Model;" Epilepsia, vol. 31 (Supp. 2) (1990), pp. S20-S26.

Liebman, K.M. et al.; "Improvement in Cognitive Function After Vagal Nerve Stimulator Implantation;" Epilepsia, vol. 39, Suppl. 6 (1998) 1 page.

Malow, B.A., et al., "Vagus Nerve Stimulation Reduces Daytime Sleepiness in Epilepsy Patients" Neurology 57 (2001) pp. 978-884.

McClintock, P., "Can Noise Actually Boost Brain Power" Physics World Jul. 2002; pp. 20-21.

Mori, T., et al.; "Noise-Induced Entrainment and Stochastic Resonance in Human Brain Waves" Physical Review Letters vol. 88, No. 21 (2002); pp. 218101-1-218101-4.

Rugg-Gunn, F.J., et al.; "Cardic Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents," IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation," Epilepsia, vol. 39, No. 7 (1998) pp. 677-686.

Tatum, W.O., et al.; "Ventricular Asystole During Vagus Nerve Stimulation for Epilepsy in Humans" American Academy of Neurologgy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Terry et al.; "The Implantable Neurocybernetic Prosthesis System", Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdez-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck, K., et al. "The Mechanism of Action Of Vagus Nerve Stimulation For Refractory Epilepsy—The Current Status", Journal of Neurophysiology, vol. 18 No. 5 (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Woodbury, et al., "Vagal Stimulation Reduces the Severity Of Maximal Electroshock Seizures in Intact Rats. Use of a Cuff Electrode for Stimulating And Recording"; Pacing and Clinical Electrophysiology, vol. 14 (Jan. 1991), pp. 94-107.

Zabara, J. "Inhibition of Experimental Seizures in Canines by Repetivie Vagal Stimulation" Epilepsia vol. 33, No. 6 (1992); pp. 1005-1012.

Dodrill, Ph.D., et al.; "Effects of Vagal Nerve Stimulation on Cognition and Quality of Life in Epilepsy;" Epilepsy and Behavior, vol. 2 (2001); pp. 46-53.

Fromes, G. A.et al.; "Clinical Utility of On-Demand Magnet use with Vagus Nerve Stimulation;" AES Proceedings, p. 117.

George, M.S., et al.; "Open Trial of VNS Therapy in Severe Anxiety Disorders;" 156th American Psychiatric Association Annual Meeting; May 17-22, 2003.

George, M.S., et al.; "Vagus Nerve Stimulation: A New Tool for Brain Research and Therapy;" Social of Biological Psychiatry vol. 47 (2000) pp. 287-295.

Fanselow, E.E., at al., "Reduction of Pentylenetetrazole-Induced Seizure Activity in Awake Rates by Seizure-Triggered Trigeminal Nerve Stimulation;" The Journal of Neuroscience, Nov. 1, 2000; vol. 20/21 ; pp. 8160-8168.

* cited by examiner

CHANGEABLE ELECTRODE POLARITY STIMULATION BY AN IMPLANTABLE MEDICAL DEVICE

CROSS REFERENCE TO RELATED APPLICATIONS

This application is a Continuation-in-Part of U.S. patent application No. 11/046,430 filed on Jan. 28, 2005 with inventors Randolph K. Armstrong and Scott A. Armstrong.

BACKGROUND OF THE INVENTION

1. Field of the Invention

This invention relates generally to medical devices, and, more particularly, to methods, apparatus, and systems for performing electrical signal therapy by a medical device.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. Nos. 4,702,254, 4,867,164, and 5,025,807 to Dr. Jacob Zabara, which are hereby incorporated in this specification in their entirety by reference.

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure. The modulation (hereinafter referred to generally as "neurostimulation" or "neuromodulation") may involve the induction of afferent action potentials, efferent action potentials, or both, in the neural structure, and may also involve blocking or interrupting the transmission of endogenous electrical activity traveling along the nerve. Electrical signal therapy or electrical modulation of a neural structure (also known as "electrical signal therapy") refers to the application of an exogenous therapeutic electrical signal (as opposed to a chemical or mechanical signal), to the neural structure. Electrical signal therapy may be provided by implanting an electrical device underneath the skin of a patient and delivering an electrical signal to a nerve such as a cranial nerve. The electrical signal therapy may involve performing a detection step, with the electrical signal being delivered in response to a detected body parameter. This type of stimulation is generally referred to as "active," "feedback," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. The stimulation may be applied by an implantable medical device that is implanted within the patient's body.

A number of medical conditions that are amenable to electrical signal therapy via cranial nerve stimulation present symptoms in regions outside the brain. For example, disorders of the neurological system, the gastrointestinal system, the pancreas, or the kidneys feature impaired or improper function of those organs. Diabetes, particularly type I diabetes, often features impaired production of insulin by the islets of Langerhans in the pancreas. Electrical signal stimulation of either the brain alone or the organ alone may have some efficacy in treating such medical conditions, but may lack maximal efficacy.

Therefore, a need exists for apparatus and methods for performing electrical signal stimulation of both the brain and an organ outside the brain. A need also exists for apparatus and methods for performing electrical signal stimulation with increased efficacy.

SUMMARY OF THE INVENTION

In one aspect, the present invention relates to a method of treating a medical condition in a patient using an implantable medical device including coupling at least a first electrode and a second electrode to a cranial nerve of the patient, providing a programmable electrical signal generator coupled to the first electrode and the second electrode, generating a first electrical signal with the electrical signal generator, applying the first electrical signal to the electrodes, wherein the first electrode is a cathode and the second electrode is an anode, reversing the polarity of the first electrode and the second electrode, yielding a configuration wherein the first electrode is an anode and the second electrode is a cathode, generating a second electrical signal with the electrical signal generator, applying the second electrical signal to the electrodes, reversing the polarity of the first electrode and the second electrode, yielding a configuration wherein the first electrode is a cathode and the second electrode is an anode, generating a third electrical signal with the electrical signal generator, and applying the third electrical signal to the electrodes.

Each of the electrical signals can independently contain one or more pulses or one or more bursts. The number of pulses need not be equal between any two of the electrical signals.

In one aspect, in a method of neuromodulation effected by delivery to a cranial nerve of an electrical signal characterized by a number of electrical pulses, the present invention relates to an improvement including delivering a first electrical signal using a first electrode as a cathode and a second electrode as an anode; reversing the polarity of the first electrode and the second electrode, yielding a configuration wherein the first electrode is an anode and the second electrode is a cathode; delivering a second electrical signal using the first electrode and the second electrode; reversing the polarity of the first electrode and the second electrode, yielding a configuration wherein the first electrode is a cathode and the second electrode is an anode; and delivering a third electrical signal using the first electrode and the second electrode.

In one aspect, the present invention relates to a system for treating a medical condition in a patient, comprising at least two electrodes coupled to at least one cranial nerve of a patient, and an implantable device operatively coupled to the electrodes and comprising an electrical signal generator capable of applying an electrical signal to the cranial nerve using the electrodes to treat the medical condition and an electrode polarity reversal unit capable of reversibly reversing the configuration of the electrodes.

BRIEF DESCRIPTION OF THE DRAWINGS

The invention may be understood by reference to the following description taken in conjunction with the accompanying drawings, in which like reference numerals identify like elements, and in which.

Figure 1A:
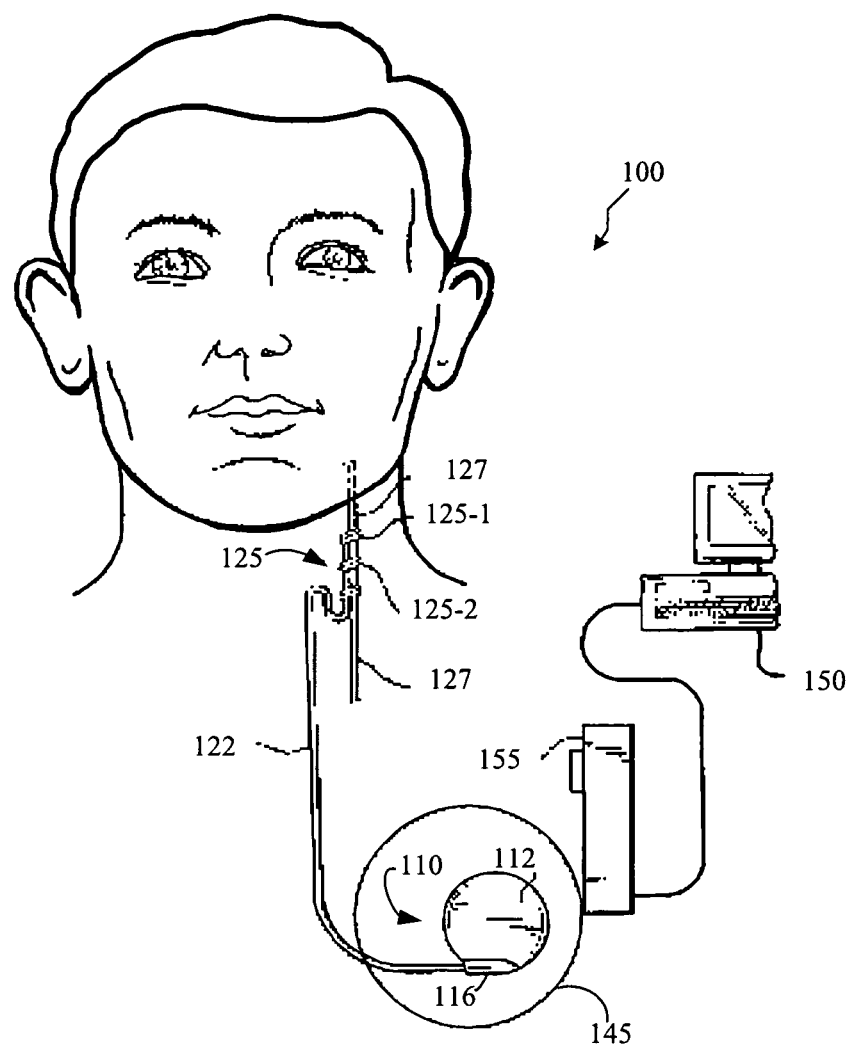
FIGS. 1A-1C provide stylized diagrams of an implantable medical device implanted into a patient's body for providing an electrical signal to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation, such as vagus nerve stimulation (VNS), has been proposed to treat a number of medical conditions pertaining to or mediated by one or more structures of the nervous system of the body, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In one embodiment, the present invention provides a method of treating a medical condition. The medical condition can be selected from the group consisting of epilepsy, neuropsychiatric disorders (including but not limited to depression), eating disorders/obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

In a further embodiment, the medical condition is selected from the group consisting of gastrointestinal disorders, pancreatic disorders, kidney disorders, and diabetes.

Figure 1B:
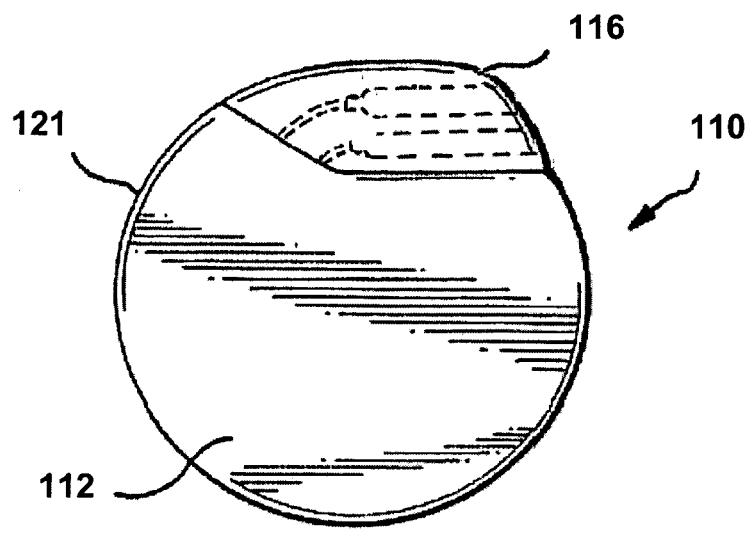
Figure 1C:
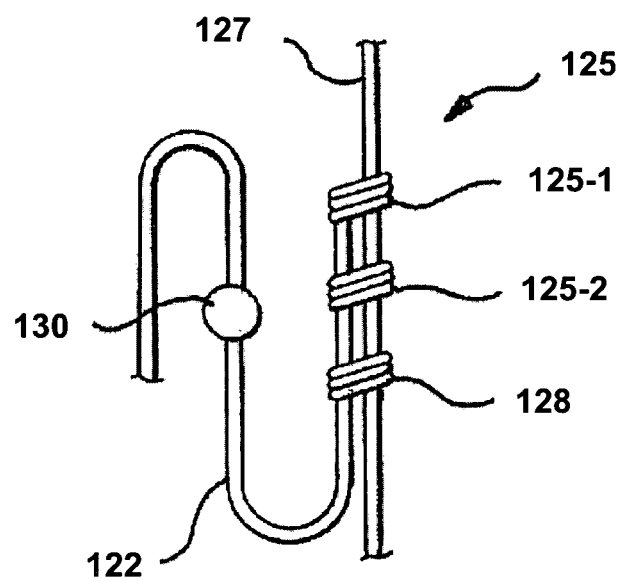

Although not so limited, a system capable of implementing embodiments of the present invention is described below. FIGS. 1A-1C depict a stylized implantable medical system 100 for implementing one or more embodiments of the present invention. FIGS. 1A-1C illustrate an electrical signal generator 110 having main body 112 comprising a case or shell 121 (FIG. 1B) with a header 116 (FIGS. 1A, 1B) for connecting to leads 122. The generator 110 is implanted in the patient's chest in a pocket or cavity formed by the implanting surgeon just below the skin (indicated by a line 145, FIG. 1A), similar to the implantation procedure for a pacemaker pulse generator.

A stimulating nerve electrode assembly 125, preferably comprising at least an electrode pair, is conductively connected to the distal end of an insulated, electrically conductive lead assembly 122, which preferably comprises a pair of lead wires (one wire for each electrode of an electrode pair). Lead assembly 122 is attached at its proximal end to connectors on the header 116 (FIG. 1B) on case 121. The electrode assembly 125 may be surgically coupled to a cranial nerve, such as vagus nerve 127 in the patient's neck or head or at another location, e.g., near the patient's diaphragm. Other cranial nerves, such as the trigeminal nerve may also be used to deliver the therapeutic electrical signal. The electrode assembly 125 preferably comprises a bipolar stimulating electrode pair 125-1, 125-2 (FIG. 1C), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention, including unipolar electrodes. Returning to FIGS. 1A and 1C, the two electrodes are preferably wrapped about the cranial nerve (e.g., vagus nerve 127), and the electrode assembly 125 may be secured to the nerve by a spiral anchoring tether 128 (FIG. 1C) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1C).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1C), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether for the electrode assembly 125.

The electrical pulse generator 110 may be programmed with an external computer 150 using programming software of a type known in the art for stimulating neural structures, or other suitable software based on the description herein, and a programming wand 155 to facilitate radio frequency (RF) communication between the computer 150 (FIG. 1A) and the pulse generator 110. The wand 155 and software permit wireless, non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in implantable medical systems 100 of the present invention. Different types of nerve fibers (e.g., A, B, and C-fibers being different fibers targeted for stimulation) respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

As used herein, the terms "stimulating" and "stimulator" may generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating", and variants thereof, are sometimes used interchangeably herein. The effect of delivery of the stimulation signal to the neural tissue may be excitatory or inhibitory and may potentiate acute and/or long-term changes in neuronal activity. For example, the effect of "stimulating" or "modulating" a neural tissue may comprise one or more of the following effects: (a) changes in neural tissue to initiate an action potential (bi-directional or uni-directional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization.

In one embodiment, the stimulation method includes the steps of generating a first electrical signal with the electrical signal generator, applying the first electrical signal to the electrodes, wherein the first electrode is a cathode and the second electrode is an anode, reversing the polarity of the first electrode and the second electrode, yielding a configuration wherein the first electrode is an anode and the second electrode is a cathode, generating a second electrical signal with the electrical signal generator, applying the second electrical signal to the electrodes, reversing the polarity of the first electrode and the second electrode, yielding a configuration wherein the first electrode is a cathode and the second electrode is an anode, generating a third electrical signal with the electrical signal generator, and applying the third electrical signal to the electrodes.

In one embodiment, the first electrical signal, the second electrical signal, and the third electrical signal are substantially identical. In another embodiment, the first electrical signal may vary from the second electrical signal, the third electrical signal, or both in terms of one or more of pulse width, number of pulses, amplitude, frequency, stimulation on-time, and stimulation off-time, among other parameters.

The first electrical signal, the second electrical signal, and the third electrical signal are described herein in terms of exemplary illustrations. The person of ordinary skill in the art having benefit of the present disclosure would appreciate that more than three electrical signals, up to an nth electrical signal, can be used and are within the scope of the present invention.

"Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to the cranial nerve. Individual pulses are separated by a time period in which no charge is delivered to the nerve, which can be called the "interpulse interval." A "burst" is used herein to refer to a plurality of pulses, wherein no charge is delivered to the nerve before the first pulse of the burst for a time period at least twice as long as the interpulse interval and no charge is delivered to the nerve after the last pulse of the burst for a time period at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

Each of the first, second, and third electrical signals can independently contain one or more pulses. In one embodiment, the first electrical signal contains one or more pulses, the second electrical signal contains one or more pulses, and the third electrical signal contains one or more pulses. In a further embodiment, the first electrical signal contains one pulse, the second electrical signal contains one pulse, and the third electrical signal contains one pulse.

The number of pulses contained within the first and second electrical signals or the second and third electrical signals need not be equal, and can be in any ratio. In one embodiment, the ratio is from about 1:100 to about 100:1. In a further embodiment, the ratio is from about 1:10 to about 10:1.

In one embodiment, the first electrical signal contains a first number of pulses, the second electrical signal contains a second number of pulses, and the third electrical signal contains a third number of pulses, wherein the first number of pulses is not equal to the second number of pulses or the second number of pulses is not equal to the third number of pulses.

In another embodiment, the first electrical signal contains one or more bursts, the second electrical signal contains one or more bursts, and the third electrical signal contains one or more bursts. In a further embodiment, the first electrical signal contains one burst, the second electrical signal contains one burst, and the third electrical signal contains one burst.

The number of bursts contained within the first and second electrical signals or the second and third electrical signals need not be equal, and can be in any ratio. In one embodiment, the ratio is from about 1:100 to about 100:1. In a further embodiment, the ratio is from about 1:10 to about 10:1.

In one embodiment, the first electrical signal contains a first number of bursts, the second electrical signal contains a second number of bursts, and the third electrical signal contains a third number of bursts, wherein the first number of bursts is not equal to the second number of bursts or the second number of bursts is not equal to the third number of bursts.

Typical cranial nerve stimulation can be performed with an interpulse frequency of 20-30 Hz (resulting in a number of pulses per burst of 140-1800, at a burst duration from 7-60 sec). In one embodiment, at least one of the first electrical signal, the second electrical signal, and the third electrical signal delivers microbursts. Microburst neurostimulation is discussed by U.S. Ser. No. 11/693,451, filed Mar. 2, 2007 and published as United States patent Publication No. 20070233193, and incorporated herein by reference. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

As stated above, different fiber types of cranial nerves propagate action potentials at different velocities. In one embodiment of the method, after performance of a prior applying step, the subsequent applying step is performed before an action potential induced by the prior applying step in C-fibers of the cranial nerve reaches the anode of the subsequent applying step and after an action potential induced by the prior applying step in A-fibers of the cranial nerve has passed the anode of the subsequent applying step. As a result, in this embodiment, an action potential induced in the A-fibers in the prior applying step can propagate along the nerve in the direction from the anode of the prior applying step to the cathode of the prior applying step and beyond to the brain or the distal terminus of the cranial nerve. Whereas, an action potential induced in the C-fibers in the prior applying step, though originally propagating along the nerve in the direction from the anode of the prior applying step to the cathode of the prior applying step, can be blocked by an electrical stimulation performed at the anode of the subsequent applying step, which was the cathode of the prior applying step. To generalize, by performing this method, particular fiber types in the cranial nerve can be selectively stimulated to propagate an action potential to either the proximal terminus (i.e., the brain) or distal terminus of the cranial nerve.

Figure 2:
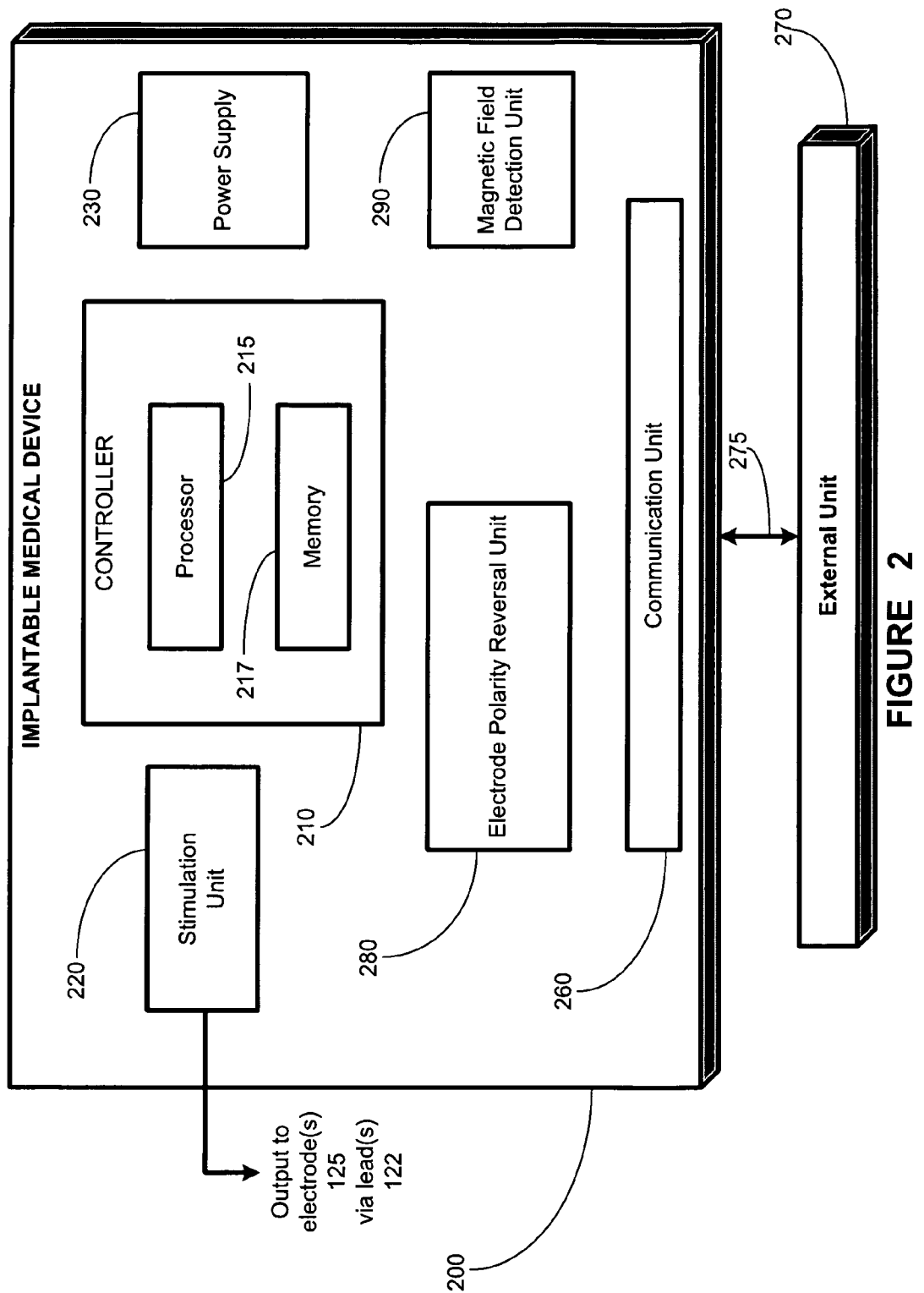
FIG. 2 illustrates a block diagram depiction of the implantable medical device of FIG. 1, in accordance with one illustrative embodiment of the present invention.

Turning now to FIG. 2, a block diagram depiction of an implantable medical device, in accordance with one illustrative embodiment of the present invention is illustrated. The IMD 200 may be coupled to various leads, e.g., 122 (FIGS. 1A, 1C). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2 (FIG. 1A). Further, signals from sensor electrodes (electrodes that are used to sense one or more body parameters such as temperature, heart rate, brain activity, etc.) may also traverse the leads back to the IMD 200.

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, or may perform stimulation based on internal calculations and programming. The controller 210 is capable of affecting substantially all functions of the IMD 200.

The controller 210 may comprise various components, such as a processor 215, a memory 217, etc. The processor 215 may comprise one or more micro controllers, micro processors, etc., that are capable of executing a variety of software components. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, primary mode electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

The IMD 200 may also comprise an electrode polarity reversal unit 280. The electrode polarity reversal unit 280 is capable of reversing the polarity of electrodes associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230, may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data to the patient, a physician, or another party.

The IMD 200 is capable of delivering stimulation that can be intermittent, periodic, random, sequential, coded, and/or patterned. The stimulation signals may comprise an electrical stimulation frequency of approximately 01 to 2500 Hz. The stimulation signals may comprise a pulse width in the range of approximately 1-2000 micro-seconds. The stimulation signals may comprise current amplitude in the range of approximately 0.1 mA to 10 mA. The stimulation delivered by the IMD 200 according to its programming may be referred to herein as "normal operations" or as a "normal operating mode."

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an inhibitory input or an excitory input from an external source. The inhibitory input may refer to an inhibition of, or a deviation from, normal stimulation operation. The excitory input may refer to additional stimulation or deviation from normal stimulation.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
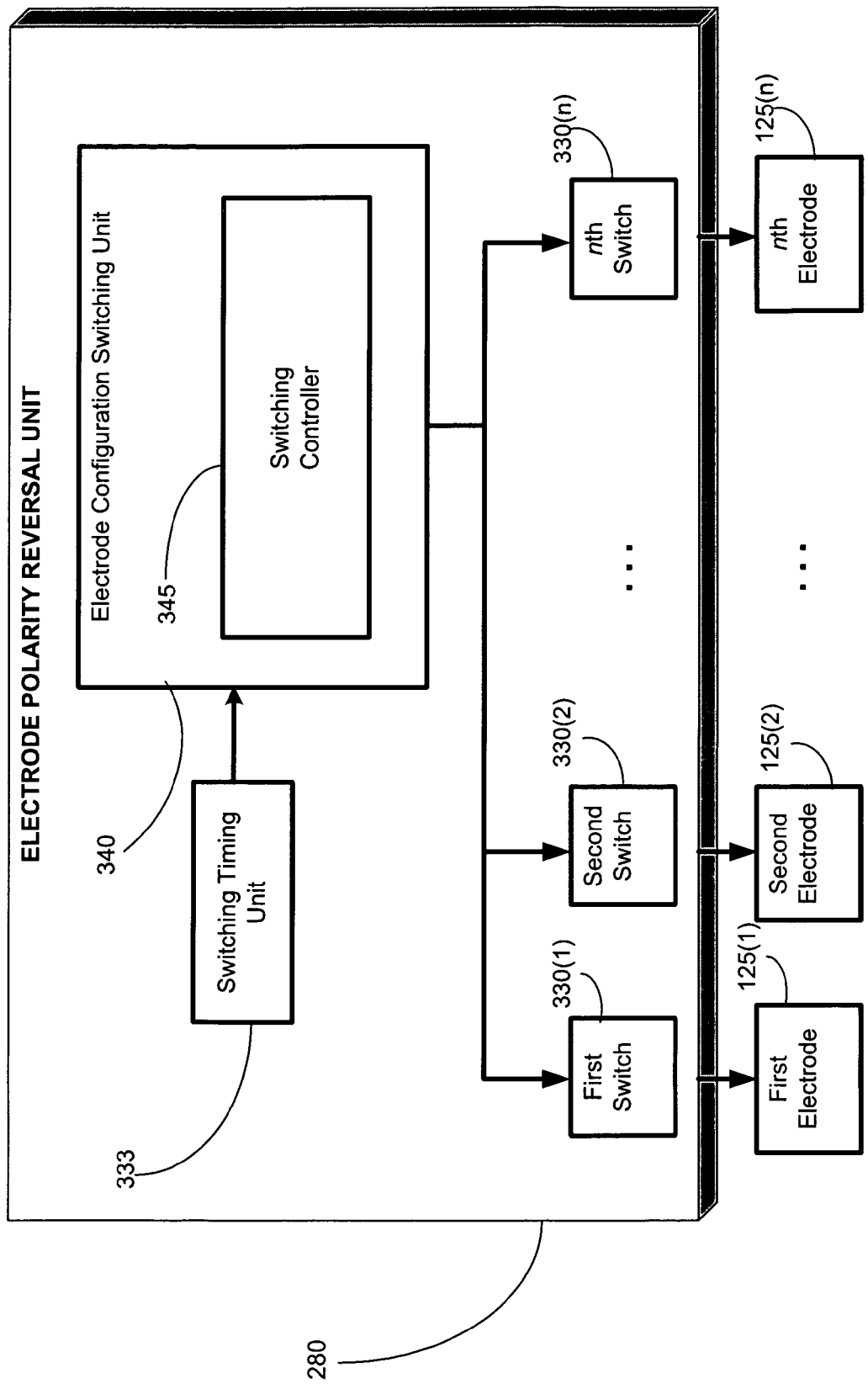
FIG. 3 illustrates a block diagram depiction of an electrode polarity reversal unit shown in FIG. 2, in accordance with one illustrative embodiment of the present invention.

FIG. 3 shows in greater detail the electrode polarity reversal unit 280 (FIG. 2). The electrode polarity reversal unit 280 comprises an electrode configuration switching unit 340, which includes a switching controller 345. The switching controller 345 transmits signals to one or more switches, generically, n switches 330(1), 330(2), . . . 330(n) which effect the switching of the configuration of two or more electrodes, generically, n electrodes 125(1), 125(2), . . . 125(n). Although FIG. 3 shows equal numbers of switches 330 and electrodes 125, the person of ordinary skill in the art having the benefit of the present disclosure will understand that the number of switches 330 and their connections with the various electrodes 125 can be varied as a matter of routine optimization. A switching timing unit 333 can signal to the electrode configuration switching unit 340 that a desired time for switching the electrode configuration has been reached.

Instructions for implementing a series of predetermined and/or programmable stimulation regimens may be stored in the IMD 200. These stimulation regimens may include data relating to the type of bidirectional stimulation to be implemented. For example, a first stimulation regimen may call for a particular type of pulse signal in one direction and having one electrode polarity configuration (e.g., an electrical signal in which action potentials to the brain are not blocked, and in which action potentials to a distal terminus of the nerve are partially or completely blocked or inhibited), followed by a plurality of microburst type signals during the normal off-time and delivered in the other direction (e.g., with the electrode polarities reversed such that action potentials to the brain are partially or completely blocked or inhibited, but action potentials to the distal terminus of the nerve are not blocked or inhibited). A second exemplary stimulation regimen may call for a series of pulses in a first direction, followed by an off-time, and then followed by a series of pulses in the opposite direction. A third exemplary stimulation regimen may call for switching electrode polarity in a 2-electrode configuration after each pulse, such that propagation of action potentials in each direction are sequentially permitted and then at least partially blocked, then permitted again in alternating sequence. In other embodiments, multiple pulses may be generated in a first electrode configuration, followed by switching electrode polarity to a second electrode configuration for one or a few pulses, followed by switching polarity back to the first electrode configuration. Information relating to the stimulation regimens may be used by the electrode polarity reversal unit 280 to control the operations of the first through nth switches 330(1-n).

In one embodiment, each of a plurality of stimulation regimens may respectively relate to a particular disorder. In one embodiment, different regimens relating to the same disorder may be implemented to accommodate improvements or regressions in the patient's present condition relative to his or her condition at previous times. By providing flexibility in electrode configurations nearly instantaneously, the present invention greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches 330(1-n) may be electrical devices, electromechanical devices, and/or solid state devices (e.g., transistors).

Figure 4:
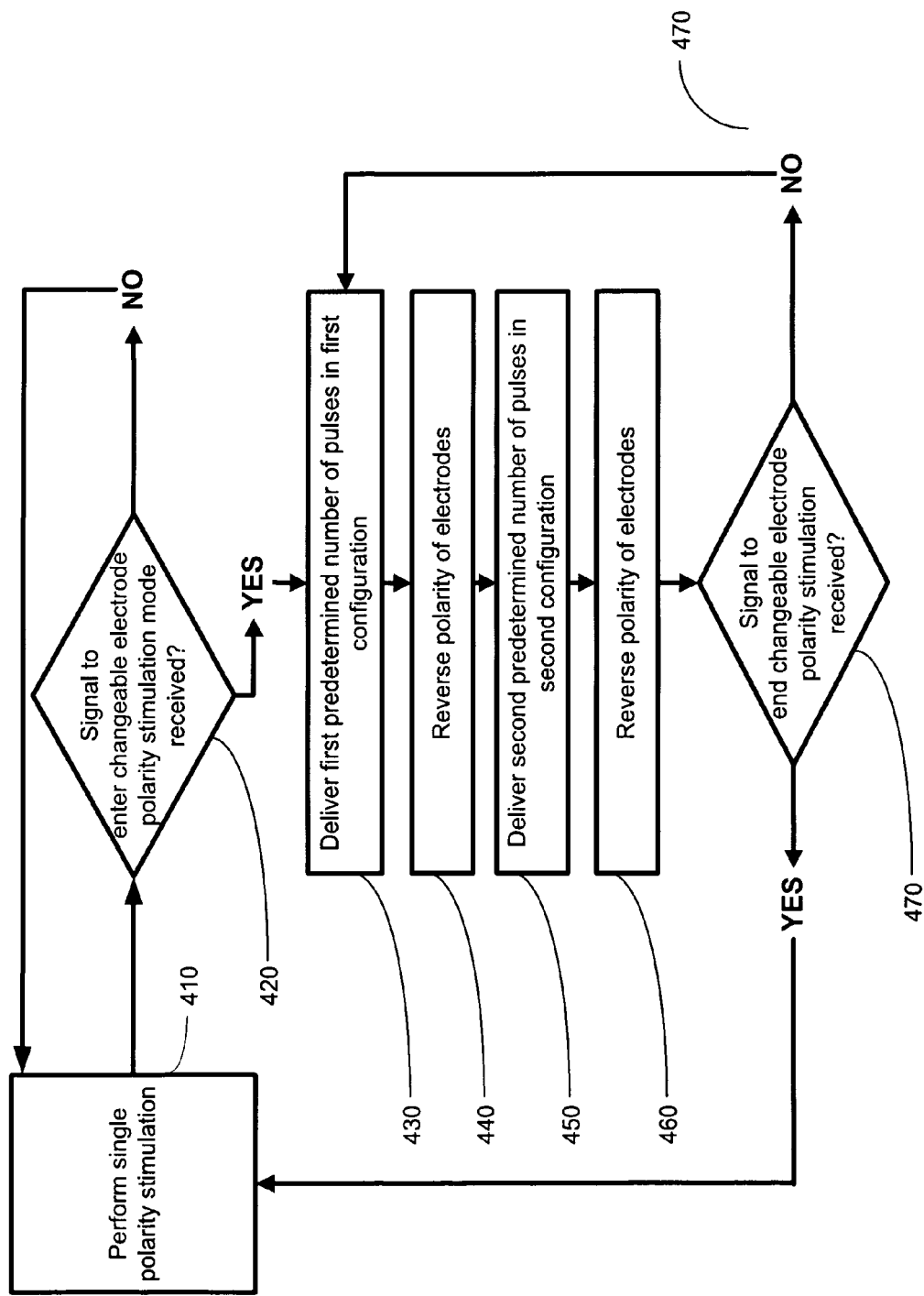
FIG. 4 illustrates a flowchart depiction of a method for performing limited patient-initiated electrical signal therapy, in accordance with an illustrative embodiment of the present invention.

FIG. 4 shows one embodiment of a method of performing changeable electrode polarity stimulation according to the present invention. In this embodiment, the IMD 200 has a first normal stimulation mode in which it performs single polarity stimulation 410, i.e., stimulation in which only one electrode 125 of the IMD 200 is the cathode for delivery of electrical signals to the cranial nerve such as vagus nerve 127, and in which the electrode polarities are only changed by manual programming. At predetermined times during performance of single polarity stimulation 410, the IMD 200 checks 420 whether a signal to enter a changeable electrode polarity stimulation mode has been received. The signal to enter a changeable electrode polarity stimulation mode can be received, by way of nonlimiting examples, from the controller 210 (FIG. 2), from a sensor or sensors implanted in or on the patient's body which detect(s) one or more bodily parameters (e.g., heart rate, respiration rate, blood pressure, blood glucose, etc.), from a medical practitioner communicating with the device via wand 155 (FIG. 1), or a medical practitioner or patient using a magnet to provide a signal via the magnetic field detection unit 290. Regardless of the nature of the signal, if the IMD 200 does not detect it when checking 420, the IMD reverts to single polarity stimulation 410.

However, if the signal is received, the IMD 200 then implements a changeable electrode polarity stimulation mode shown in steps 430-460. Specifically, the IMD 200 delivers 430 a first predetermined number of pulses in a first polarity configuration of the electrodes. For an example, a first electrode 125(1) may be the cathode and a second electrode 125(2) may be the anode in step 430. After the first predetermined number of pulses are delivered in the first configuration (step 430), the IMD 200 reverses 440 the polarity of the electrodes to a second polarity configuration. Continuing the example, the first electrode 125(1) may be switched to be the anode and the second electrode 125(2) may be switched to be the cathode. It will be appreciated that, where 3 or more electrodes are used, only some of the electrode polarities may be reversed. Step 450 resembles step 430, though it will be noted the second electrode polarity configuration differs from the first electrode polarity configuration, and the second predetermined number of pulses may differ in number of pulses or other stimulation parameters (pulse frequency, pulse width, On Time, Off Time, interpulse interval, number of pulses per burst, or interburst interval, among others) from the first predetermined number of pulses. Step 460 resembles step 440, though it will be noted it reverts the configuration of the electrodes to the first electrode polarity configuration as in step 430.

After steps 430-460 have been performed, the IMD 200 checks 470 whether a signal to discontinue the changeable electrode polarity stimulation mode has been received. The signal to discontinue the changeable electrode polarity stimulation mode can be received from the same sources described above in the context of checking step 420. Regardless of the nature of the signal, if the IMD 200 does not detect the signal when performing checking step 470, the IMD 200 continues changeable electrode polarity stimulation by returning to step 430. If the signal is detected when performing checking step 470, the IMD 200 reverts to single polarity stimulation 410.

Figure 5:
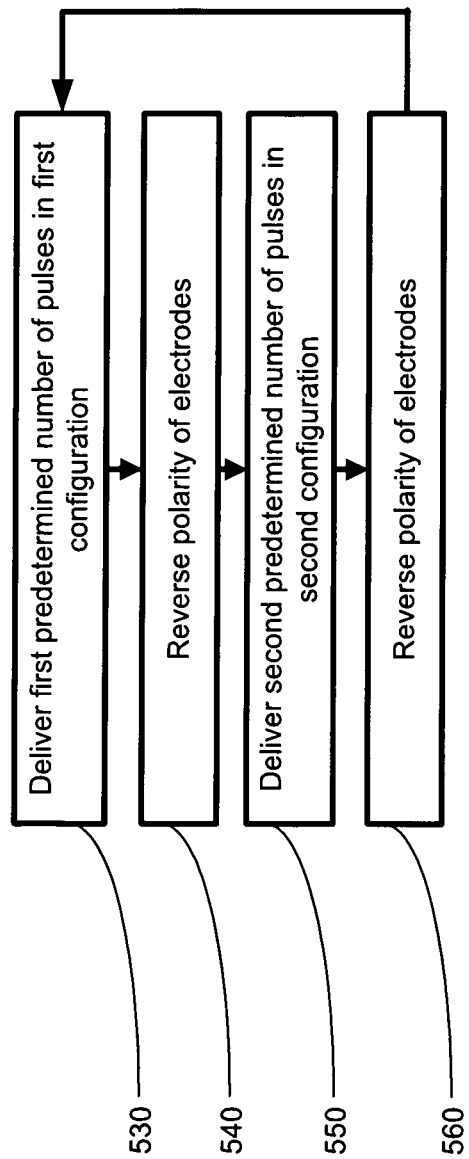
FIG. 5 illustrates a flowchart depiction of a method for performing limited patient-initiated electrical signal therapy, in accordance with another illustrative embodiment of the present invention.

FIG. 5 shows another embodiment of a method according to the present invention. The method comprises steps 530-560, which resemble steps 430-460 shown in FIG. 4. The method shown in FIG. 5 does not include single polarity stimulation; after the second reversal step 560 is performed, the IMD 200 continues changeable electrode polarity stimulation by returning to step 530.

In the methods shown in FIGS. 4-5, one or more of the properties of the first predetermined number of pulses (e.g., number of pulses, pulse frequency, pulse width, On time, Off time, interpulse interval, number of pulses per burst, or interburst interval, among others) can be changed upon each performance of step 430 or 530. The properties can be varied in a preprogrammed fashion, following programming executed by the controller 210, or can be varied according to data retrieved from a sensor of a bodily parameter of the patient or in response to instructions received from a medical practitioner or the patient. Similarly, one or more of the properties of the second predetermined number of pulses can be changed upon each performance of step 450 or 550.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method of treating one or more medical conditions in a patient, the method comprising:
    applying a first electrical signal in a first stimulation mode to a cranial nerve of the patient, via at least first and second electrodes coupled to an electrical signal generator of an implantable medical device and to the cranial nerve, wherein the first electrode operates as a cathode and is proximal to a brain relative to the second electrode that operates as an anode and is distal to the brain, wherein the first stimulation mode performs single polarity stimulation;
    receiving an output from a sensor configured to detect one or more bodily parameters of the patient;
    entering a second stimulation mode based on the output received from the sensor, wherein the second stimulation mode performs changeable electrode polarity stimulation;
    applying a second electrical signal in the second stimulation mode to the cranial nerve of the patient, via the first and second electrodes, wherein the first and second electrodes are configured to switch between a first electrode configuration and a second electrode configuration in the second stimulation mode, wherein the first electrode operates as the cathode and the second electrode operates as the anode in the first electrode configuration, wherein the first electrode operates as the anode and the second electrode operates as the cathode in the second electrode configuration.

2. The method of claim 1, wherein the first electrical signal contains one pulse and the second electrical signal contains one pulse.

3. The method of claim 1, wherein the first electrical signal contains a first number of pulses and the second electrical signal contains a second number of pulses, wherein: the first number of pulses is not equal to the second number of pulses.

4. The method of claim 1, wherein the first electrical signal contains one burst and the second electrical signal contains one burst.

5. The method of claim 1, wherein the first electrical signal contains a first number of bursts and the second electrical signal contains a second number of bursts,
    the first number of bursts is not equal to the second number of bursts.

6. The method of claim 1, wherein the second electrical signal is characterized by having an interpulse interval in a range from about 2 milliseconds to about 4.3 milliseconds for each centimeter of distance between the first electrode and the second electrode.

7. The method of claim 1, wherein at least one of the first electrical signal and the second electrical signal is characterized by having a number of pulses per microburst from 2 pulses to about 25 pulses, an interpulse interval of about 2 milliseconds to about 50 milliseconds, an interburst period of at least 100 milliseconds, and a microburst duration of less than about 1 second.

8. The method of claim 1, wherein the medical condition being treated is at least one of a neurological disorder, neuropsychiatric disorder, gastrointestinal disorder, pancreatic disorder, kidney disorder, or diabetes.

9. The method of claim 1, wherein the cranial nerve is a vagus nerve.

10. The method of claim 1, wherein applying the first electrical signal to the cranial nerve treats a first medical condition of the brain.

11. The method of claim 1, wherein applying the second electrical signal to the cranial nerve treats a non-brain medical condition.

12. An implantable medical device to treat medical conditions in a patient, the implantable medical device comprising:
    a controller configured to receive an output from a sensor configured to detect one or more bodily parameters of the patient;
    a stimulation unit coupled to the controller, the stimulation unit configured to generate and deliver electrical signals to a cranial nerve of the patient via first and second electrodes coupled to the cranial nerve, wherein the stimulation unit is configured to deliver a first electrical signal in a first stimulation mode to the cranial nerve via the first electrode and the second electrode, the first electrode operating as a cathode and proximal to a brain relative to the second electrode, the second electrode operating as an anode and distal to the brain, wherein the first stimulation mode performs single polarity stimulation;
    wherein the controller is configured to enter a second stimulation mode based on the output received from the sensor, wherein the second stimulation mode performs changeable electrode polarity stimulation;
    wherein the stimulation unit is configured to deliver a second electrical signal to the cranial nerve, via the first and second electrodes, wherein the first and second electrodes are configured to switch between a first electrode configuration and a second electrode configuration in the second stimulation mode, wherein the first electrode operates as the cathode and the second electrode operates as the anode in the first electrode configuration, wherein the first electrode operates as the anode and the second electrode operates as the cathode in the second electrode configuration.

13. The implantable medical device of claim 12, wherein the first electrical signal contains one pulse and the second electrical signal contains one pulse.

14. The implantable medical device of claim 12, wherein the first electrical signal contains a first number of pulses and the second electrical signal contains a second number of pulses, wherein
    the first number of pulses is not equal to the second number of pulses.

15. The implantable medical device of claim 12, wherein the first electrical signal contains one burst and the second electrical signal contains one burst.

16. The implantable medical device of claim 12, wherein the first electrical signal contains a first number of bursts and the second electrical signal contains a second number of bursts, wherein
    the first number of bursts is not equal to the second number of bursts.

17. The implantable medical device of claim 12, wherein the stimulation unit is configured to provide for an interpulse interval, between delivery of the first electrical signal and the second electrical signal, in a range from about 2 milliseconds to about 4.3 milliseconds for each centimeter of distance between the first electrode and the second electrode.

18. The implantable medical device of claim 12, wherein at least one of the first electrical signal and the second electrical signal is characterized by having a number of pulses per microburst from 2 pulses to about 25 pulses, an interpulse interval of about 2 milliseconds to about 50 milliseconds, an interburst period of at least 100 milliseconds, and a microburst duration of less than about 1 second.

19. The implantable medical device of claim 12, wherein the medical condition being treated is at least one of a neurological disorder, neuropsychiatric disorder, gastrointestinal disorder, pancreatic disorder, kidney disorder, or diabetes.

20. The implantable medical device of claim 12, wherein the cranial nerve is a vagus nerve.

21. The implantable medical device of claim 12, wherein delivering the first electrical signal to the cranial nerve treats a first medical condition of the brain.

22. The implantable medical device of claim 12, wherein delivering the second electrical signal to the cranial nerve treats a non-brain medical condition.

23. A method of treating at least one medical condition in a patient, the method comprising:

applying a first electrical signal in a first stimulation mode to a cranial nerve of the patient, via at least first and second electrodes coupled to an electrical signal generator of an implantable medical device and to the cranial nerve, wherein the first electrode operates as a cathode and is proximal to a brain relative to the second electrode that operates as an anode and is distal to the brain, wherein the first stimulation mode performs single polarity stimulation;

receiving an output from a sensor configured to detect one or more bodily parameters of the patient, the one or more bodily parameters including at least one of heart rate, respiration rate, blood pressure, and blood glucose;

entering a second stimulation mode based on the output received from the sensor, wherein the second stimulation mode performs changeable electrode polarity stimulation;

applying a second electrical signal in the second stimulation mode to the cranial nerve of the patient, via the first and second electrodes coupled to the electrical signal generator and to the cranial nerve, wherein the first and second electrodes are configured to switch between a first electrode configuration and a second electrode configuration in the second stimulation mode, wherein the first electrode operates as the cathode and the second electrode operates as the anode in the first electrode configuration, wherein the first electrode operates as the anode and the second electrode operates as the cathode in the second electrode configuration.

* * * * *